(12) United States Patent
Akiba et al.

(10) Patent No.: US 9,931,027 B2
(45) Date of Patent: Apr. 3, 2018

(54) VIDEO PROCESSOR

(71) Applicant: OLYMPUS CORPORATION, Hachioji-shi, Tokyo (JP)

(72) Inventors: Hirotaka Akiba, Tokyo (JP); Hiroyuki Ushifusa, Tokyo (JP); Daisuke Sano, Yokohama (JP); Hiroshi Tamai, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/671,442

(22) Filed: Aug. 8, 2017

(65) Prior Publication Data

US 2017/0332889 A1 Nov. 23, 2017

Related U.S. Application Data

(63) Continuation of application No. PCT/JP2016/064158, filed on May 12, 2016.

(30) Foreign Application Priority Data

May 25, 2015 (JP) ................................ 2015-105904

(51) Int. Cl.
*F21V 7/04* (2006.01)
*A61B 1/05* (2006.01)
(Continued)

(52) U.S. Cl.
CPC ............ *A61B 1/05* (2013.01); *A61B 1/00009* (2013.01); *A61B 1/0669* (2013.01); *G02B 23/26* (2013.01)

(58) Field of Classification Search
CPC ..... A61B 1/05; A61B 1/00009; A61B 1/0669; G02B 23/26
(Continued)

(56) References Cited

U.S. PATENT DOCUMENTS

2002/0026098 A1* 2/2002 Kobayashi ......... A61B 1/00009
600/160

FOREIGN PATENT DOCUMENTS

JP     S63-189820 A    8/1988
JP     2001-149303 A   6/2001
(Continued)

OTHER PUBLICATIONS

Aug. 2, 2016 International Search Report issued in International Patent Application No. PCT/JP2016/064158.
(Continued)

*Primary Examiner* — Anh Mai
*Assistant Examiner* — Hana Featherly
(74) *Attorney, Agent, or Firm* — Oliff PLC (57) ABSTRACT

A video processor that is connectable to an endoscope and an external light source device that supplies illumination light to a light guide of the endoscope includes: a connection detector that detects a presence/absence of connection between the video processor and the light guide of the endoscope; an internal light source unit that supplies the illumination light to the light guide of the endoscope; a communication controller that performs communication with the external light source device, and obtains device data of the external light source device; and a utilized light source determination unit that determines a light source that supplies the illumination light to the light guide of the endoscope in accordance with a detection result of the connection detector or a state of obtainment of the device data of the communication controller.

6 Claims, 8 Drawing Sheets

(51) Int. Cl.
    *A61B 1/00*   (2006.01)
    *A61B 1/06*   (2006.01)
    *G02B 23/26*  (2006.01)
(58) Field of Classification Search
    USPC .......................................................... 362/618
    See application file for complete search history.

(56) References Cited

FOREIGN PATENT DOCUMENTS

| JP | 2010-011894 A | 1/2010 |
| JP | 2011-087680 A | 5/2011 |
| JP | 2012-183240 A | 9/2012 |

OTHER PUBLICATIONS

Aug. 2, 2016 Written Opinion issued in International Patent Application No. PCT/JP2016/064158.
Mar. 28, 2017 Office Action issued in Japanese Patent Application No. 2017-512846.
May 16, 2017 Office Action issued in Japanese Patent Application No. 2017-512846.

* cited by examiner

VIDEO PROCESSOR

CROSS-REFERENCE TO RELATED APPLICATIONS

This application is based upon and claims the benefit of priority of the prior Japanese Patent Application No. 2015-105904, filed May 25, 2015, the entire contents of which are incorporated herein by reference.
This is a Continuation Application of PCT Application No. PCT/JP2016/064158, filed May 12, 2016, which was not published under PCT Article 21(2) in English.

FIELD

The present invention relates to a video processor that includes an image processing unit that processes image data obtained by an endoscope and a light source unit that supplies illumination light to the endoscope.

BACKGROUND

Conventionally, as an image processing device that processes image data obtained by an endoscope, a light source integrated type image processing device has been proposed that is configured so as to be integrated with a light source device that supplies illumination light to a light guide of the endoscope. In addition, examples of the light source integrated type image processing device above include a device that an external light source device can be further connected to and a device that the external light source device cannot be connected to.

In a light source integrated type image processing device that an external light source device can be connected to, a function that cannot be used in an internal light source device can be used by connecting the external light source device.

In this case, the switching of a light source to be used (switching from the internal light source device to the external light source device), and setting relating to, for example, the adjustment of an amount of illumination light that is supplied to the light guide of the endoscope by the external light source device, are manually performed.

As an endoscope system that includes a light source integrated type image processing device that an external light source device can be connected to, an electronic endoscope system disclosed in Japanese Laid-Open Patent Publication No. 2012-183240 is known, for example. This electronic endoscope system is an electronic endoscope system that can automatically change settings to an appropriate white balance parameter even when a light source to be used is changed, and the electronic endoscope system has the following configuration. An electronic endoscope includes a storage provided with a plurality of areas that store a white balance setting value, and the storage stores a white balance setting value for an internal light source of a processor and a white balance setting value for a first external light source. The processor includes a first light guide connection detector that detects a state of connection between a light guide and the processor, and the first external light source includes a second light guide connection detector that detects a state of connection between the light guide and the first external light source, and a detection result transmitter that transmits a detection result to the processor. In addition, the processor further includes a detection result receiver that receives the detection result from the detection result transmitter, and a color tone adjuster that changes a white balance to a white balance that is suitable for a light source that is determined to be being utilized in accordance with detection results of the first and second light guide connection detectors so as to adjust a color tone of image data.

SUMMARY

In an aspect of the present invention, a video processor is provided that is connectable to an endoscope and an external light source device that supplies illumination light to a light guide of the endoscope. The video processor includes: a connection detector that detects a presence/absence of connection between the video processor and the light guide of the endoscope; an internal light source unit that supplies the illumination light to the light guide of the endoscope; a communication controller that performs communication with the external light source device, and obtains device data of the external light source device; and a utilized light source determination unit that determines a light source that supplies the illumination light to the light guide of the endoscope in accordance with a detection result of the connection detector or a state of obtainment of the device data of the communication controller. The utilized light source determination unit performs: determining that the internal light source unit is a light source being utilized, when the light guide of the endoscope is connected to the video processor; determining that an external light source device that is communicable with the video processor is being utilized, when the communication controller obtains the device data in a state in which the light guide of the endoscope is not connected to the video processor; and determining that an external light source device that is not communicable with the video processor is being utilized, when the communication controller fails to obtain the device data in a state in which the light guide of the endoscope is not connected to the video processor.

DESCRIPTION OF EMBODIMENTS

Embodiments of the present invention are described below with reference to the drawings.

First Embodiment

A video processor according to a first embodiment of the present invention is included, for example, in an endoscope system used in endoscopy in medical institutions (hospitals or the like).

Figure 1:
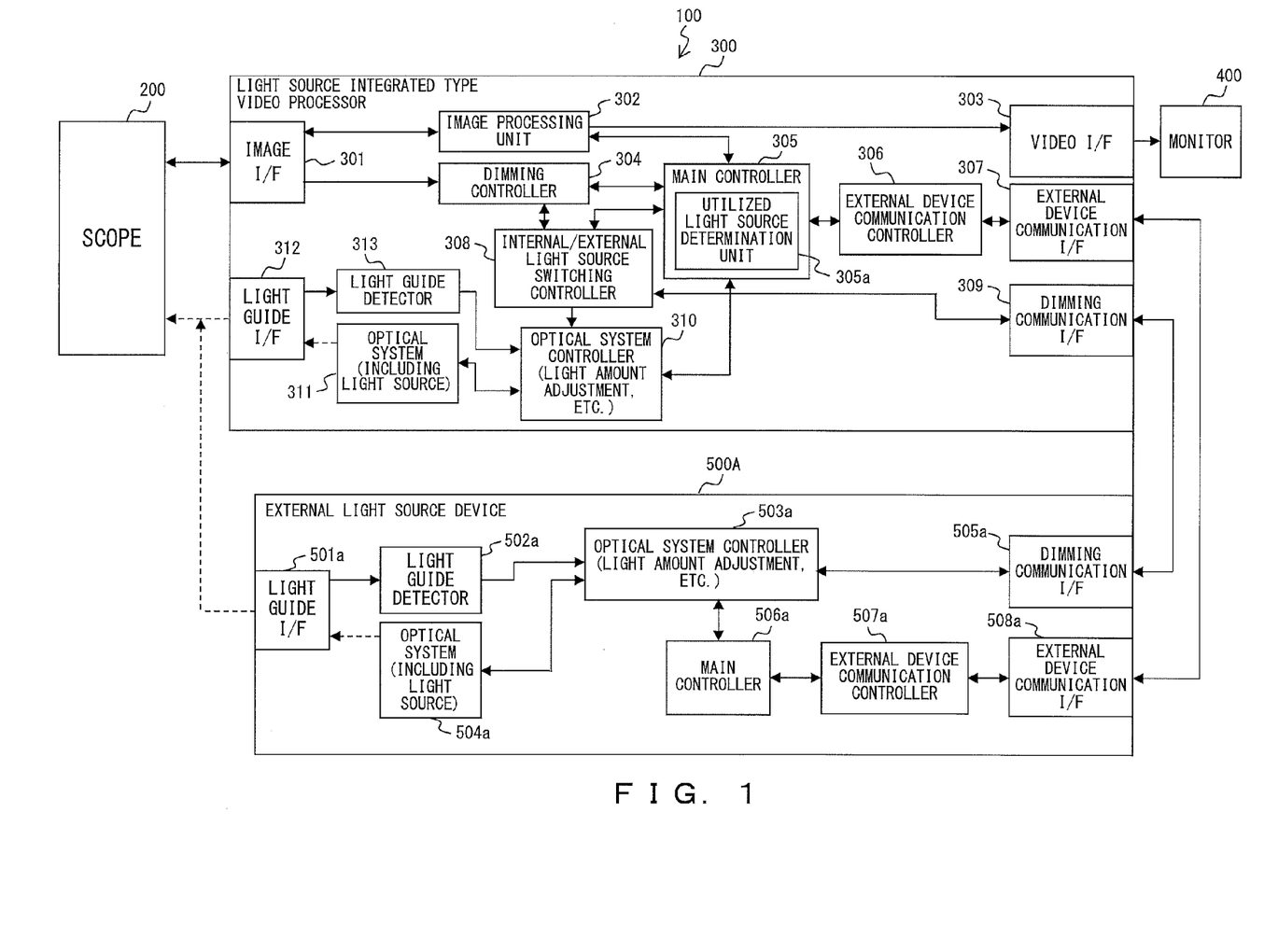
FIG. 1 illustrates a first exemplary configuration of an endoscope system that includes a light source integrated type video processor that is a video processor according to a first embodiment.
Figure 2:
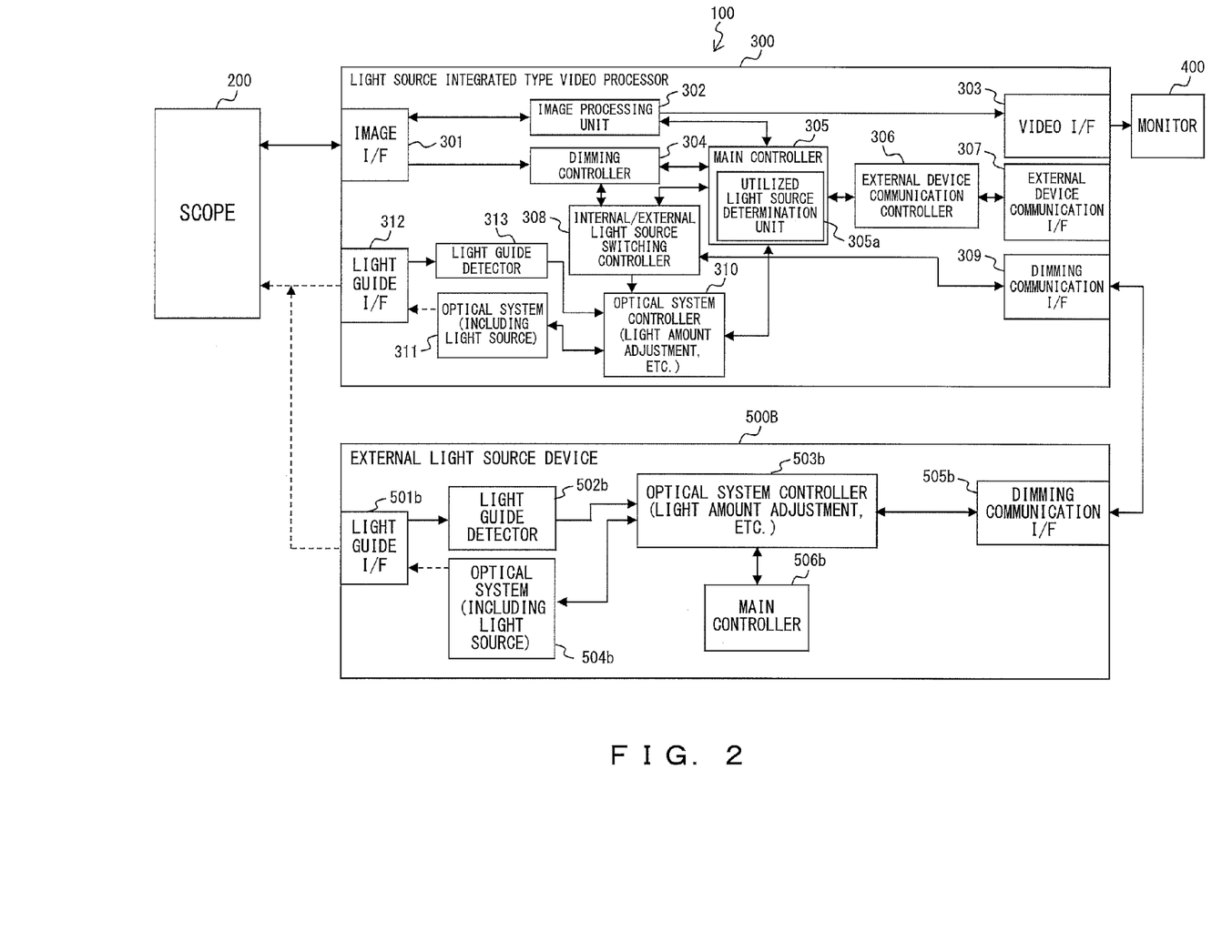
FIG. 2 illustrates a second exemplary configuration of the endoscope system that includes the light source integrated type video processor that is the video processor according to the first embodiment.

FIG. 1 and FIG. 2 illustrate exemplary configurations of an endoscope system that includes a light source integrated type video processor that is a video processor according to this embodiment. More specifically, FIG. 1 illustrates an exemplary configuration of an endoscope system that includes, as an external light source device, an external light source device that can perform communication with the video processor. FIG. 2 illustrates an exemplary configuration of an endoscope system that includes, as an external light source device, an external light source device that cannot perform communication (excluding communication relating to dimming control) with the video processor.

As illustrated in FIG. 1 and FIG. 2, an endoscope system 100 according to this embodiment includes a scope (an endoscope) 200, a video processor 300, a monitor 400, and an external light source device 500 (500A (see FIG. 1) or 500B (see FIG. 2)).

The scope 200 images the inside of a subject (the inside of a body of an examinee) so as to obtain image data of the inside of the subject, and outputs the image data to the video processor 300 connected to the scope 200. In addition, the scope 200 guides illumination light that is supplied from the video processor 300 or the external light source device 500 (500A or 500B) that is connected to a not-illustrated light guide of the scope 200 to the inside of the subject, and illuminates the inside of the subject. Further, the scope 200 performs communication with the video processor 300 connected to the scope 200.

The video processor 300 includes an image interface (I/F) 301, an image processing unit 302, a video I/F 303, a dimming controller 304, a main controller 305, an external device communication controller 306, an external device communication I/F 307, an internal/external light source switching controller 308, a dimming communication I/F 309, an optical system controller 310, an optical system 311, a light guide I/F 312, and a light guide detector 313.

The image I/F 301 is a connector to which the scope 200 is connected. An input of image data from the scope 200 to the video processor 300 and communication between the scope 200 and the video processor 300 are performed via the image I/F 301.

The image processing unit 302 processes the image data input from the scope 200 via the image I/F 301 so as to generate a video signal, and outputs the video signal to the monitor 400 via the video I/F 303.

The video I/F 303 is a connector to which the monitor 400 is connected.

The dimming controller 304 generates dimming control data according to an internal light source or dimming control data according to an external light source on the basis of the image data input from the scope 200 via the image I/F 301, and outputs the dimming control data to the internal/external light source switching controller 308. The dimming control data is data for setting an amount of illumination light applied to the inside of the subject. The dimming control data according to the internal light source is dimming control data according to the optical system 311, and the dimming control data according to the external light source is dimming control data according to an optical system 504 (504a or 504b) of the external light source device 500 (500A or 500B). The dimming control data according to the external light source is generated on the basis of the image data input from the scope 200 via the image I/F 301, and state data of the optical system 504a of the external light source device 500A and device data of the external light source device 500A, or state data of the optical system 504b of the external light source device 500B. The state data of the optical system 504 (504a or 504b) of the external light source device 500 (500A or 500B) is input from the external light source device 500 (500A or 500B) via the dimming communication I/F 309 and the internal/external light source switching controller 308 to the dimming controller 304. In addition, the device data of the external light source device 500A is input from the external light source device 500A via the external device communication I/F 307, the external device communication controller 306, and the main controller 305 to the dimming controller 304.

The main controller 305 controls the entire operation of the video processor 300. As an example, the main controller 305 performs communication with the scope 200 via the image processing unit 302 and the image I/F 301. In addition, the main controller 305 performs communication with an external device (in this example, the external light source device 500A) via the external device communication controller 306 and the external device communication I/F 307. In communication with the external device, the main controller 305 obtains the device data of the external light source device 500A, a detection result (the presence/absence of connection to a light guide) of a light guide detector 502a, and the like from the external light source device 500A. Further, the main controller 305 obtains a detection result (the presence/absence of connection to a light guide) of the light guide detector 313 via the optical system controller 310. Furthermore, the main controller 305 includes a utilized light source determination unit 305a that determines a light source being utilized.

The external device communication controller 306 controls communication with an external device (in this example, the external light source device 500A) that is connected to the external device communication I/F 307 under the control of the main controller 305.

The external device communication I/F 307 is a connector to which an external device (in this example, the external light source device 500A) is connected. Communication between the video processor 300 and the external light source device 500A (excluding communication relating to dimming control) is performed via the external device communication I/F 307.

The internal/external light source switching controller 308 switches an output destination of the dimming control data generated by the dimming controller 304 to the optical system controller 310 or the dimming communication I/F 309 under the control of the main controller 305. In addition, the internal/external light source switching controller 308 performs communication relating to dimming control with the external light source device 500 (500A or 500B) via the dimming communication I/F 309. In communication relating to dimming control, the internal/external light source switching controller 308 outputs the dimming control data to the external light source device 500 (500A or 500B), or obtains the state data of the optical system 504 (504*a* or 504*b*) of the external light source device 500 (500A or 500B). Further, the internal/external light source switching controller 308 outputs the obtained state data to the dimming controller 304 (and the main controller 305 as needed).

The dimming communication I/F 309 is a connector to which the external light source device 500 (500A or 500B) is connected. Communication relating to dimming control between the video processor 300 and the external light source device 500 (500A or 500B) is performed via the dimming communication I/F 309.

The optical system controller 310 controls the optical system 311 according to the dimming control data input from the internal/external light source switching controller 308, a detection result indicating the type of a light guide that has been input from the light guide detector 313, and a state data of the optical system 311 that has been input from the optical system 311, under the control of the main controller 305, and performs dimming (the adjustment of alight amount) or the like of illumination light emitted from the optical system 311. In addition, the optical system controller 310 outputs, to the main controller 305, a detection result indicating the presence/absence of connection to a light guide that has been input from the light guide detector 313. Further, the optical system controller 310 outputs, to the main controller 305, the state data of the optical system 311 that has been input from the optical system 311.

The optical system 311 includes a not-illustrated light source, and emits illumination light according to the control of the optical system controller 310. The light source included in the optical system 311 is a light source that includes an LED of each color, such as R (Red), G (Green), B (Blue), or V (Violet). In addition, the optical system 311 detects a state (such as an amount of light emitted from each of the LEDs) of the optical system 311, and outputs the state data to the optical system controller 310. The amount of light emitted from each of the LEDs is detected, for example, by a not-illustrated photosensor that is included in the optical system 311.

The light guide I/F 312 is a connector to which a light guide of the scope 200 is connected. Illumination light is supplied from the video processor 300 to the scope 200 via the light guide I/F 312.

The light guide detector 313 detects whether the light guide of the scope 200 is connected to the light guide I/F 312, and outputs a detection result to the optical system controller 310. The light guide detector 313 detects the type (such as a light guide for a high luminance or a light guide for a standard luminance) of the light guide connected to the light guide I/F 312, and outputs a detection result to the optical system controller 310. The light guide detector 313 may perform the detection above by using, for example, a photosensor (a photo-interrupter or the like), a mechanical switch (a push switch or the like), or an electrical contact. In this case, as an example, the shape of a connector of the light guide connected to the light guide I/F 312 may be configured so as to change according to the type of the light guide, and a difference in the shape of the connector may be detected by using the photosensor or the mechanical switch. As another example, an electrical contact for which a pattern changes according to the type of the light guide may be provided in the connector of the light guide connected to the light guide I/F 312, and a difference in the pattern of the electrical contact may be detected according to the presence/absence of conduction with an electrical contact having a prescribed pattern that has been provided in advance in the light guide I/F 312.

The monitor 400 displays video according to a video signal that is input from the video processor 300 connected to the monitor 400.

The external light source device 500A includes a light guide I/F 501*a*, a light guide detector 502*a*, an optical system controller 503*a*, an optical system 504*a*, a dimming communication I/F 505*a*, a main controller 506*a*, an external device communication controller 507*a*, and an external device communication I/F 508*a*.

The external light source device 500B includes a light guide I/F 501*b*, a light guide detector 502*b*, an optical system controller 503*b*, an optical system 504*b*, a dimming communication I/F 505*b*, and a main controller 506*b*.

The light guide I/F 501*a*, the light guide detector 502*a*, the optical system controller 503*a*, the optical system 504*a*, the dimming communication I/F 505*a*, and the main controller 506*a* in the external light source device 500A have configurations similar to those of the light guide I/F 501*b*, the light guide detector 502*b*, the optical system controller 503*b*, the optical system 504*b*, the dimming communication I/F 505*b*, and the main controller 506*b* in external light source device 500B. Accordingly, only the configurations of the components above in the external light source device 500A are representatively described below, and description of the configurations of the components above in the external light source device 500B is omitted.

The light guide I/F 501*a* is a connector to which the light guide of the scope 200 is connected. Illumination light is supplied from the external light source device 500A to the scope 200 via the light guide I/F 501*a*.

The light guide detector 502*a* detects whether the light guide of the scope 200 is connected to the light guide I/F 501*a*, and outputs a detection result to the optical system controller 503*a*. In addition, the light guide detector 502*a* detects the type (such as alight guide for a high luminance or a light guide for a standard luminance) of the light guide connected to the light guide I/F 501*a*, and outputs a detection result to the optical system controller 503*a*. The light guide detector 502*a* may perform the detection above by using, for example, a photosensor, a mechanical switch, or an electrical contact, similarly to the light guide detector 313 described above.

The optical system controller 503*a* controls the optical system 504*a* according to dimming control data input from the dimming communication I/F 505*a* and the detection result indicating the type of the light guide that has been input from the light guide detector 502*a* under the control of the main controller 506*a*, and performs, for example, dimming (the adjustment of a light amount) of illumination light emitted by the optical system 504*a*. In addition, the optical system controller 503*a* outputs, to the main controller 506*a*, a detection result indicating the presence/absence of connection to a light guide that has been input from the light guide detector 502*a*. Further, the optical system controller 503*a* performs communication relating to dimming control with the video processor 300 via the dimming communication I/F 505*a*. In communication relating to dimming control, the optical system controller 503*a* obtains dimming control data from the video processor 300, or outputs, to the video processor 300, state data of the optical system 504*a* that has been input from the optical system 504*a*.

The optical system 504*a* includes a light source and a shutter that are not illustrated, and emits illumination light according to the control of the optical system controller 503a. The light source included in the optical system 504a is, for example, a Xenon lamp light source. In addition, the optical system 504a detects a state (such as the position of the shutter or an amount of light emitted from the Xenon lamp light source) of the optical system 504a, and outputs state data to the optical system controller 503a. The position of the shutter is detected, for example, by a not-illustrated position sensor included in the optical system 504a, and the amount of light emitted from the Xenon lamp light source is detected, for example, by a not-illustrated photosensor included in the optical system 504a.

The dimming communication I/F 505a is a connector to which the video processor 300 is connected. Communication relating to dimming control between the external light source device 500A and the video processor 300 is performed via the dimming communication I/F 505a.

The main controller 506a controls the entire operation of the external light source device 500A. As an example, the main controller 506a performs communication with an external device (in this example, the video processor 300) via the external device communication controller 507a and the external device communication I/F 508a. In communication with the video processor 300, the main controller 506a outputs, to the video processor 300, device data of the external light source device 500A, a detection result (the presence/absence of connection to a light guide) of the light guide detector 502a, and the like. Examples of the device data of the external light source device 500A include a device identification (ID) of the external light source device 500A, and data relating to a light source included in the external light source device 500A (a light source included in the optical system 504a) (data relating to the type of the light source, a total utilized time, or the like). In addition, the main controller 506a outputs other data such as device information (a device model number, a serial number, and the like) of the external light source device 500A to the video processor 300 in communication with the video processor 300 via the external device communication controller 507a and the external device communication I/F 508a. The main controller 506a also outputs, for example, information needed to control the external light source device 500A on a side of the video processor 300 (information indicating setting of an observation mode, (automatic or manual) setting of dimming, or the like). In this case, the external light source device 500A can be remotely controlled by using a keyboard or the like that is connected to the video processor 300. In addition, the main controller 506a outputs information, such as an operation log or an error log, that has been recorded in the external light source device 500A. In this case, the information above is stored on a side of the video processor 300.

The main controller 506b of the external light source device 500B does not perform communication (excluding communication relating to dimming control) with an external device, because the external light source device 500B does not include the external device communication controller 507a and the external device communication I/F 508a.

The external device communication controller 507a controls communication with an external device (in this example, the video processor 300) that is connected to the external device communication I/F 508a under the control of the main controller 506a.

The external device communication I/F 508a is a connector to which an external device (in this example, the video processor 300) is connected. Communication between the external light source device 500A and the video processor 300 (excluding communication relating to dimming control) is performed via the external device communication I/F 508a.

In the video processor 300 included in the endoscope system 100 having the configuration above, the image processing unit 302 is an example of an image processing unit that processes image data obtained by an endoscope. The light guide detector 313 is an example of a connection detector that detects the presence/absence of connection between the video processor and a light guide of the endoscope. The optical system 311 including a light source and the optical system controller 310 are an example of an internal light source unit that supplies illumination light to the light guide of the endoscope. The dimming controller 304 is an example of a dimming controller that generates dimming control data that controls an amount of illumination light supplied to the light guide of the endoscope. The internal/external light source switching controller 308 is an example of a switching unit that switches an output destination of the dimming control data to an internal light source unit or an external light source device that is provided outside the video processor and that supplies illumination light to the light guide of the endoscope, in accordance with a detection result of the connection detector.

In addition, in the endoscope system 100, the controllers and the processing unit described above that are included in the video processor 300, and the controllers above included in each of the external light source devices 500A and 500B are configured, for example, by circuits such as application specific integrated circuits (ASICs) or field programmable gate arrays (FPGAs). Alternatively, each of the video processor 300 and the external light source devices 500A and 500B may include, for example, a processor such as a CPU and a memory, and the processor may execute a program stored in the memory such that functions of the controllers and the processing unit described above that are included in the video processor 300 and functions of the controllers above included in each of the external light source devices 500A and 500B are realized.

The operation of the endoscope system 100 according to this embodiment is described next.

Here, as an example of the operation, a light source switching operation performed by the video processor 300 is described.

Figure 3A:
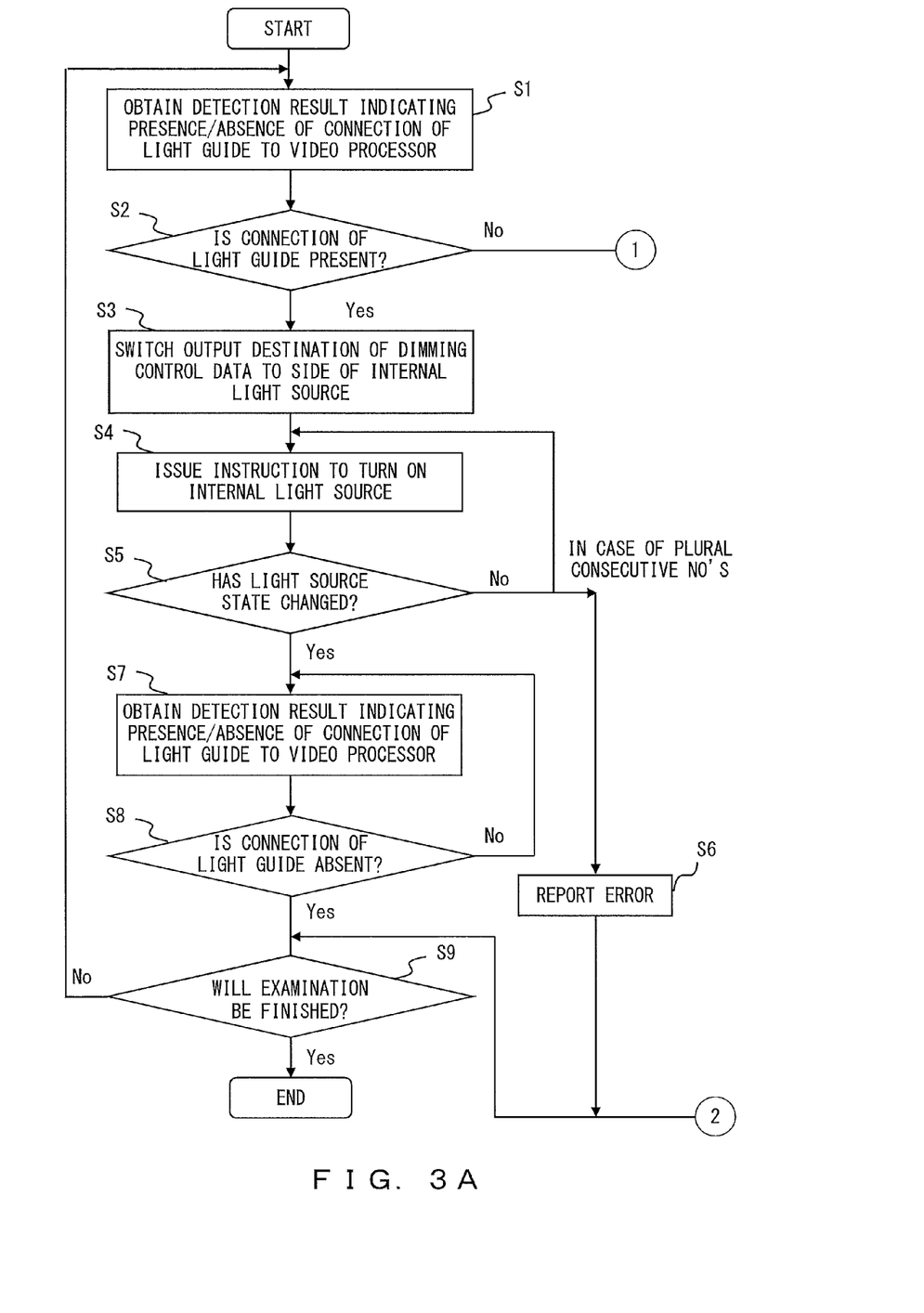
FIG. 3A is a first flowchart illustrating an example of a light source switching operation performed by the light source integrated type video processer that is the video processor according to the first embodiment.
Figure 3B:
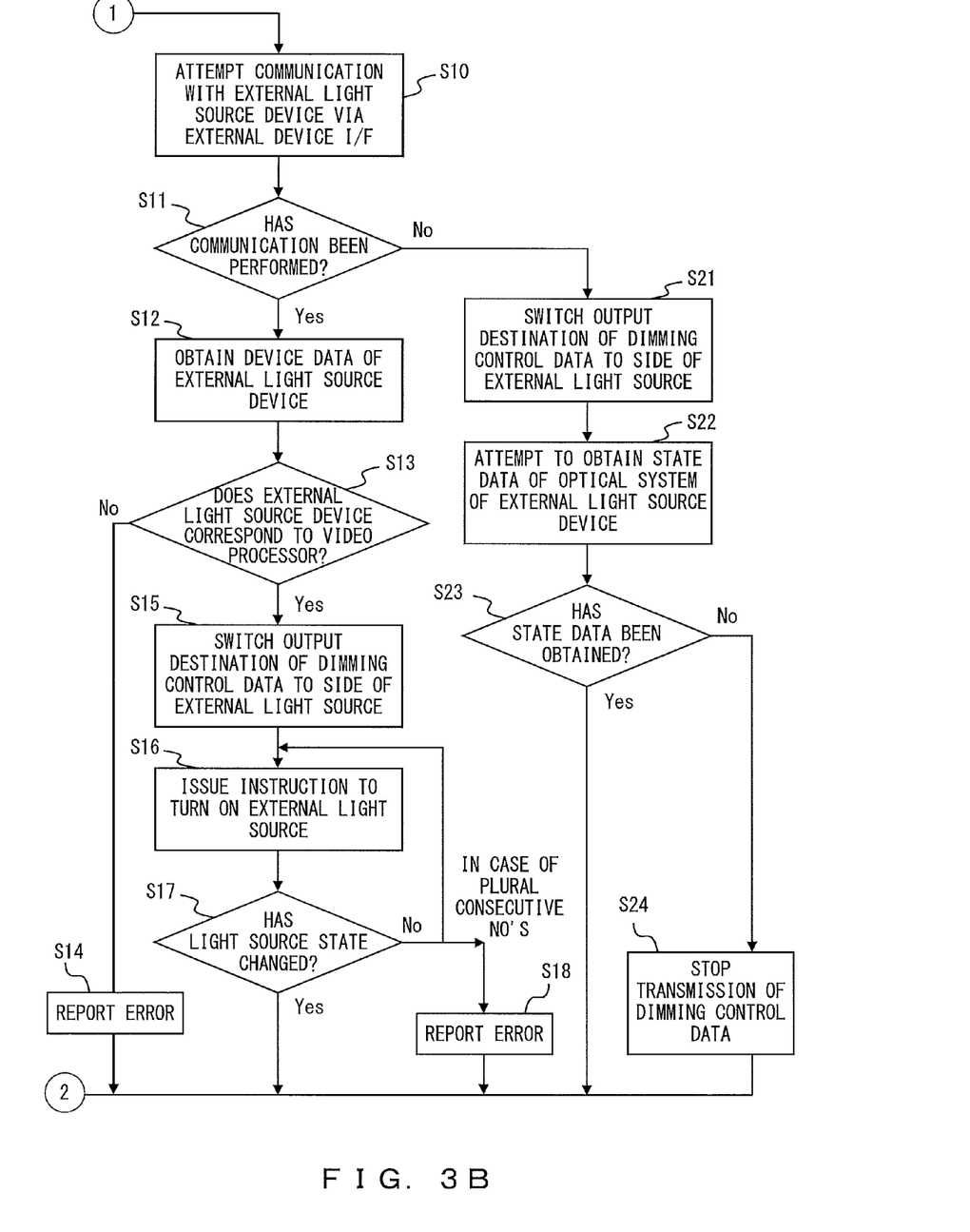
FIG. 3B is a second flowchart illustrating an example of a light source switching operation performed by the light source integrated type video processer that is the video processor according to the first embodiment.

FIG. 3 (FIG. 3A and FIG. 3B) is a flowchart illustrating an example of the light source switching operation. This operation is performed, for example, during endoscopy.

As illustrated in FIG. 3, when this operation is started, first, the main controller 305 obtains a detection result of the light guide detector 313 that indicates the presence/absence of connection to a light guide, via the optical system controller 310 (S1).

The main controller 305 determines whether a light guide is connected to the video processor 300 in accordance with the detection result obtained in S1 (S2).

When the determination result in S2 is Yes, the internal/external light source switching controller 308 switches an output destination of dimming control data generated by the dimming controller 304 to the optical system controller 310 (on a side of an internal light source) under the control of the main controller 305 (S3). The dimming control data generated by the dimming controller 304 is dimming control data according to the internal light source that is generated by the dimming controller 304 under the control of the main controller 305. When the determination result in S2 is Yes, the utilized light source determination unit 305a included in the main controller 305 determines that the internal light source is a light source being utilized.

The main controller 305 issues an instruction to turn on the internal light source to the optical system controller 310 (S4). In response to the instruction to turn on the internal light source, the optical system controller 310 controls the optical system 311 in accordance with the dimming control data input from the internal/external light source switching controller 308, a detection result indicating the type of the light guide that has been input from the light guide detector 313, and state data of the optical system 311 that has been input from the optical system 311. In this control, dimming (the adjustment of a light amount) of illumination light emitted from the optical system 311 is performed, for example.

The main controller 305 determines whether a state of the light source of the optical system 311 has changed (for example, whether the state has changed from the turn-off state to the turn-on state) in accordance with the state data of the optical system 311 that is input from the optical system 311 via the optical system controller 310 (S5).

When the determination result in S5 is No, the processing returns to S4. When the determination result in S5 becomes No plural consecutive times, the main controller 305 issues an error report (for example, a report indicating an abnormality of the internal light source) (S6), and the processing moves on to S9. The error report is issued, for example, by displaying an error screen on a not-illustrated display unit in the video processor 300 or the monitor 400.

When the determination result in S5 is Yes, the main controller 305 obtains the detection result of the light guide detector 313 that indicates the presence/absence of connection to a light guide via the optical system controller 310 again (S7).

The main controller 305 determines whether a light guide is unconnected to the video processor 300 in accordance with the detection result obtained in S7 (S8).

When the determination result in S8 is No, the processing returns to S7.

When the determination result in S8 is Yes, the main controller 305 determines whether endoscopy has been finished (S9). The determination is performed, for example, according to whether an instruction to finish endoscopy has been input via a not-illustrated operation unit in the video processor 300.

When the determination result in S9 is No, the processing returns to S1, and when the determination result in S9 is Yes, this operation is terminated.

When the determination result in S2 is No, the main controller 305 attempts communication with an external light source device via the external device communication controller 306 and the external device communication I/F 307 (S10).

The main controller 305 determines whether communication has been performed with the external light source device via the external device communication controller 306 and the external device communication I/F 307 (S11).

When the determination result in S11 is Yes, the main controller 305 obtains device data of the external light source device from the external light source device via the external device communication controller 306 and the external device communication I/F 307 (S12). When the determination result in S11 is Yes, the utilized light source determination unit 305a included in the main controller 305 determines that an external light source that is communicable with the video processor 300 is a light source being utilized.

The main controller 305 determines whether the external light source device is an external light source device that corresponds to the video processor 300 in accordance with the device data obtained in S12 (S13). The external light source device that corresponds to the video processor 300 refers to an external light source device that can be controlled by the video processor 300 (for example, an external light source device on which dimming control can be performed by the video processor 300).

When the determination result in S13 is No, the main controller 305 issues an error report (for example, a report indicating that the external light source device does not correspond to the video processor 300) (S14), and the processing moves on to S9. The error report is issued, for example, by displaying an error screen on a not-illustrated display unit in the video processor 300 or the monitor 400, similarly to the process of S6 described above.

When the determination result in S13 is Yes (when the external light source device 500A is connected to the video processor 300), the internal/external light source switching controller 308 switches an output destination of dimming control data generated by the dimming controller 304 to the dimming communication I/F 309 (on a side of the external light source) under the control of the main controller 305 (S15). The dimming control data generated by the dimming controller 304 is dimming control data according to the external light source that has been generated by the dimming controller 304 under the control of the main controller 305.

The main controller 305 issues an instruction to turn on the external light source to the external light source device 500A via the external device communication controller 306 and the external device communication I/F 307 (S16). In response to the instruction to turn on the external light source that has been issued from the video processor 300 via the dimming communication I/F 505a, the optical system controller 503a of the external light source device 500A controls the optical system 504a in accordance with dimming control data that has been input from the video processor 300 via the dimming communication I/F 505a, a detection result indicating the type of a light guide that has been input from the light guide detector 502a, and state data of the optical system 504a that has been input from the optical system 504a. In this control, dimming (the adjustment of a light amount) of illumination light emitted from the optical system 504a is performed, for example.

The main controller 305 determines whether a state of a light source of the optical system 504a has changed (for example, whether the state has changed from the turn-off state to the turn-on state) in accordance with the state data of the optical system 504a that has been input from the external light source device 500A via the dimming communication I/F 309 and the internal/external light source switching controller 308 (S17).

When the determination result in S17 is No, the processing returns to S16. When the determination result in S17 becomes No plural consecutive times, the main controller 305 issues an error report (for example, a report indicating an abnormality of a light source of the external light source device 500A) (S18), and the processing moves on to S9. The error report is issued, for example, by displaying an error screen on a not-illustrated display unit in the video processor 300 or the monitor 400, similarly to the process of S6 described above.

When the determination result in S17 is Yes, the processing moves on to S9.

When the determination result in S11 is No, the internal/external light source switching controller 308 switches an output destination of dimming control data generated by the dimming controller 304 to the dimming communication I/F 309 (on a side of the external light source) under the control of the main controller 305 (S21). The dimming control data generated by the dimming controller 304 is dimming control data according to the external light source that has been generated by the dimming controller 304 under the control of the main controller 305. When the determination result in S11 is No, the utilized light source determination unit 305a included in the main controller 305 determines that an external light source that is incommunicable with the video processor 300 is a light source being utilized.

The main controller 305 attempts to obtain state data of an optical system from the external light source device via the dimming communication I/F 309 and the internal/external light source switching controller 308 (S22).

The main controller 305 determines whether the state data of the optical system has been obtained from the external light source device (S23).

When the determination result in S23 is Yes (when the external light source device 500B is connected to the video processor 300), the processing moves on to S9. In this case, the optical system controller 503b of the external light source device 500B controls the optical system 504b in accordance with dimming control data that has been input from the video processor 300 via the dimming communication I/F 505b, a detection result indicating the type of a light guide that has been input from the light guide detector 502b, and state data of the optical system 504b that has been input from the optical system 504b. In this control, dimming (the adjustment of a light amount) of illumination light emitted from the optical system 504b is performed, for example.

When the determination result in S23 is No, the main controller 305 stops transmission of the dimming control data from the video processor 300 to the external light source device (S24), and the processing moves on to S9.

In the operation illustrated in FIG. 3, the processing after the determination result in S2 becomes No before the processing returns to S1 again is not illustrated, but the light guide detector 313 continues to detect the presence/absence of connection. When a detection result indicates the presence of connection, the processing returns to S1.

When the determination result in S2 becomes Yes, and communication with an external light source device is performed successfully (namely, when both an internal light source and the external light source device are detected), a light source is switched in such a way that a light source to be used preferentially becomes the internal light source.

In the operation above of FIG. 3, the switching of a light source to be used, and setting relating to the adjustment of a light amount (dimming) of illumination light supplied to a light guide (the generation of dimming control data) are automatically performed according to whether the light guide is connected to the video processor 300 regardless of whether an external light source device (the external light source device 500 (500A or 500B) or another external light source device) is connected to the video processor 300. Stated another way, when the light guide is connected to the video processor 300, a light source is switched in such a way that a light source to be used becomes an internal light source (a light source in the video processor 300), and setting relating to the adjustment of an amount of illumination light according to the internal light source (the generation of dimming control data) is automatically performed. When the light guide is not connected to the video processor 300, a light source is switched in such a way that a light source to be used becomes an external light source (a light source in the external light source device 500 (500A or 500B)), and setting relating to the adjustment of an amount of illumination light according to the external light source (the generation of dimming control data) is automatically performed.

As described above, by employing the video processor according to this embodiment, the switching of a light source to be used, and setting relating to the adjustment of an amount of illumination light supplied to a light guide can be automatically performed, and therefore a burden on a user associated with switching and setting can be reduced.

Second Embodiment

A video processor according to a second embodiment of the present invention is different from the video processor according to the first embodiment in some components and some operations. Differences will be principally described in description of the video processor according to the second embodiment. The same component as the component described in the first embodiment is denoted by the same reference numeral.

Figure 4:
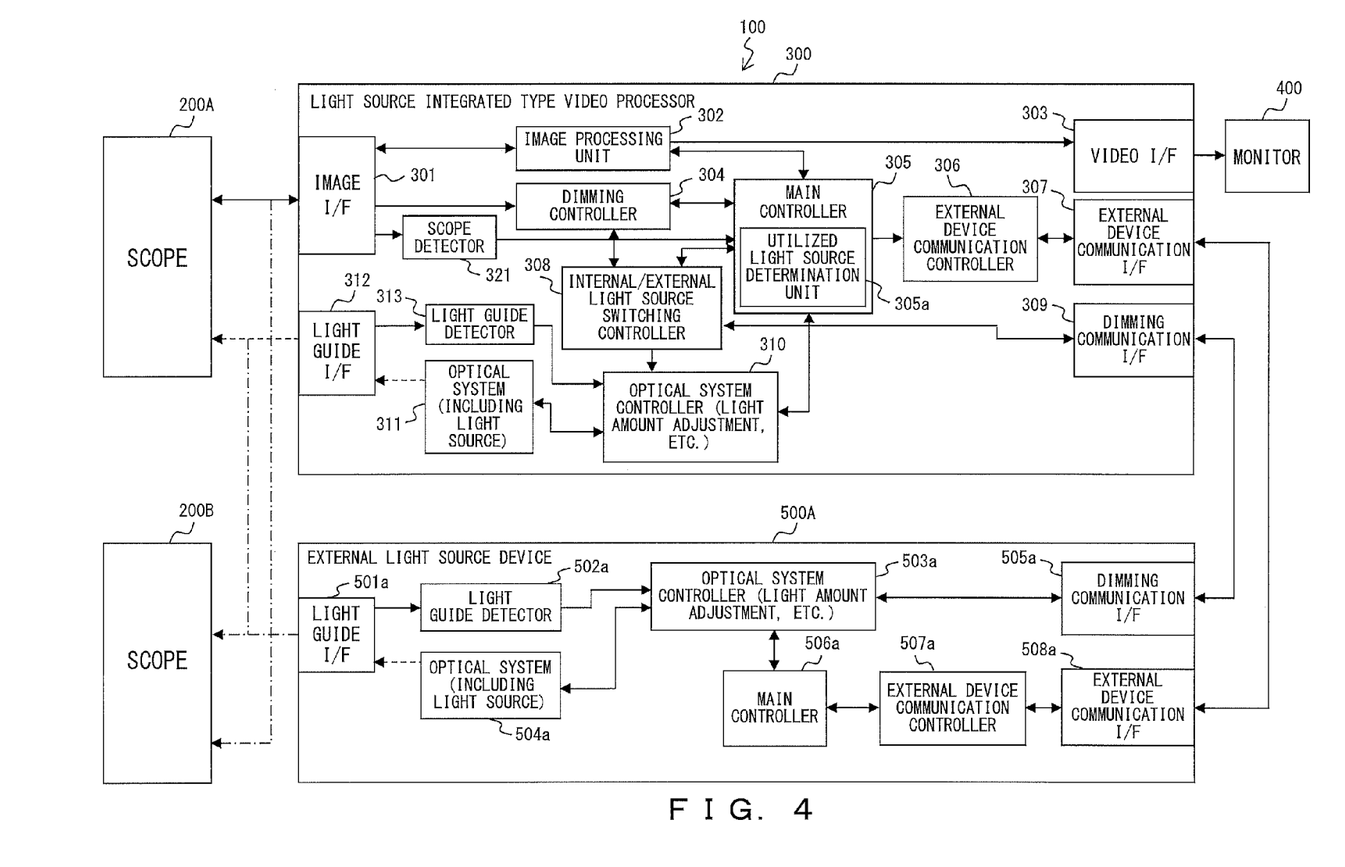
FIG. 4 illustrates an exemplary configuration of an endoscope system that includes a light source integrated type video processor that is a video processor according to a second embodiment.

FIG. 4 illustrates an exemplary configuration of an endoscope system including the video processor according to the second embodiment.

An endoscope system 100 illustrated in FIG. 4 is different from the endoscope system 100 illustrated in FIG. 1 in that the endoscope system 100 illustrated in FIG. 4 includes two types of scopes 200A and 200B as the scope 200 and in that the video processor 300 further includes a scope detector 321.

The endoscope system 100 according to this embodiment may be configured so as to include the external light source device 500B instead of the external light source device 500A, similarly to the endoscope system 100 illustrated in FIG. 2.

The two types of scopes 200A and 200B include different image sensors that image the inside of a subject. More specifically, the scope 200A includes an image sensor for which the number of pixels is large (hereinafter referred to as a "high-pixel-number image sensor"), and the scope 200B includes an image sensor for which the number of pixels is smaller than that of the image sensor of the scope 200A (hereinafter referred to as a "standard-pixel-number image sensor"). Assume that the size of an image sensor is the same in both of the scopes.

The scope detector 321 of the video processor 300 detects whether the scope 200 (200A or 200B) is connected to the image I/F 301, and outputs a detection result to the main controller 305. The scope detector 321 may perform the detection above by using, for example, a photosensor, a mechanical switch, or an electrical contact, similarly to the light guide detector 313 described above.

When the main controller 305 receives a detection result indicating that the scope 200 (200A or 200B) is connected to the image I/F 301 from the scope detector 321, the main controller 305 obtains scope data from the scope 200 (200A or 200B) via the image I/F 301 and the image processing unit 302. The scope data includes a scope ID and image sensor data that indicates, for example, whether an image sensor is a high-pixel-number image sensor or a standard-pixel-number image sensor. The main controller 305 outputs, to the dimming controller 304, the image sensor data that is included in the scope data obtained from the scope 200 (200A or 200B).

The dimming controller 304 generates dimming control data according to an internal light source on the basis of the image sensor data input from the main controller 305, and image data input from the scope 200 via the image I/F 301. The dimming controller 304 also generates dimming control data according to an external light source on the basis of the image sensor data input from the main controller 305, the image data input from the scope 200 via the image I/F 301, state data of the optical system 504a of the external light source device 500A, and device data of the external light source device 500A (or state data of the optical system 504b of the external light source device 500B).

By doing this, the dimming controller 304 can generate dimming control data in such away that an amount of illumination light changes according to the image sensor data. As an example, in a case in which the image sensor data indicates a high-pixel-number image sensor, dimming control data can be generated in such a way that an amount of illumination light is smaller than in a case in which the image sensor data indicates a standard-pixel-number image sensor. The generation above of the dimming control data is performed without adversely affecting image quality. By doing this, an amount of illumination light is reduced, and therefore the lifetime of a light source can be prolonged, and power consumption can be reduced.

In this embodiment, the dimming control data has been described to be data that controls an amount of illumination light, but the dimming control data is not limited to this. As an example, the dimming control data may be data that adjusts a gain relating to the brightness of image data, or may be data that controls a shutter speed of an optical system.

The endoscope system 100 illustrated in FIG. 4 is similar to the endoscope system 100 illustrated in FIG. 1 in the other respects.

In the video processor 300 included in the endoscope system 100 according to this embodiment, the main controller 305 is an example of an endoscopic data obtaining unit that obtains endoscopic data relating to an endoscope connected to the video processor.

The operation of the endoscope system 100 according to this embodiment is described next.

As an example of the operation, a light source switching operation performed by the video processor 300 according to this embodiment is described below.

Figure 5A:
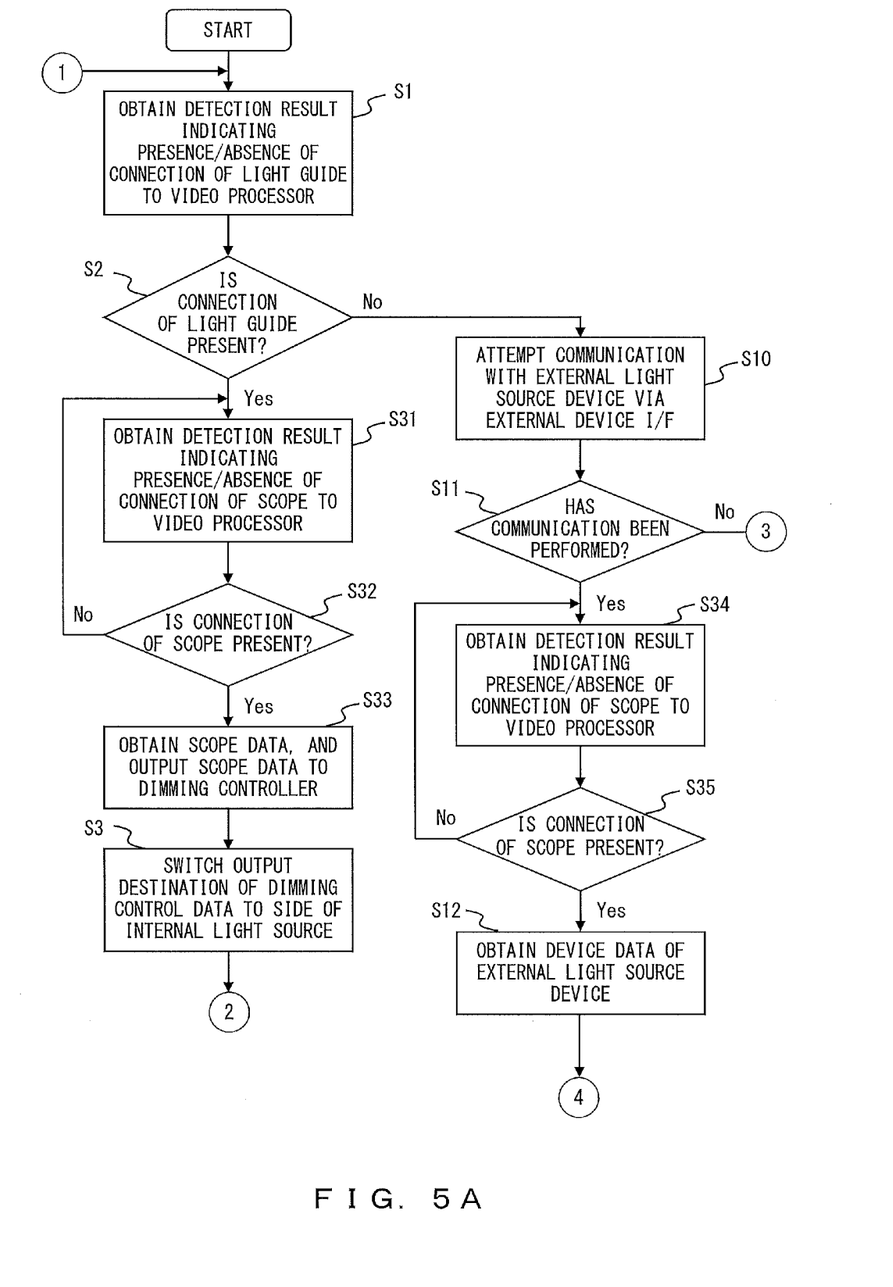
FIG. 5A is a first flowchart illustrating an example of a light source switching operation performed by the light source integrated type video processor that is the video processor according to the second embodiment.
Figure 5B:
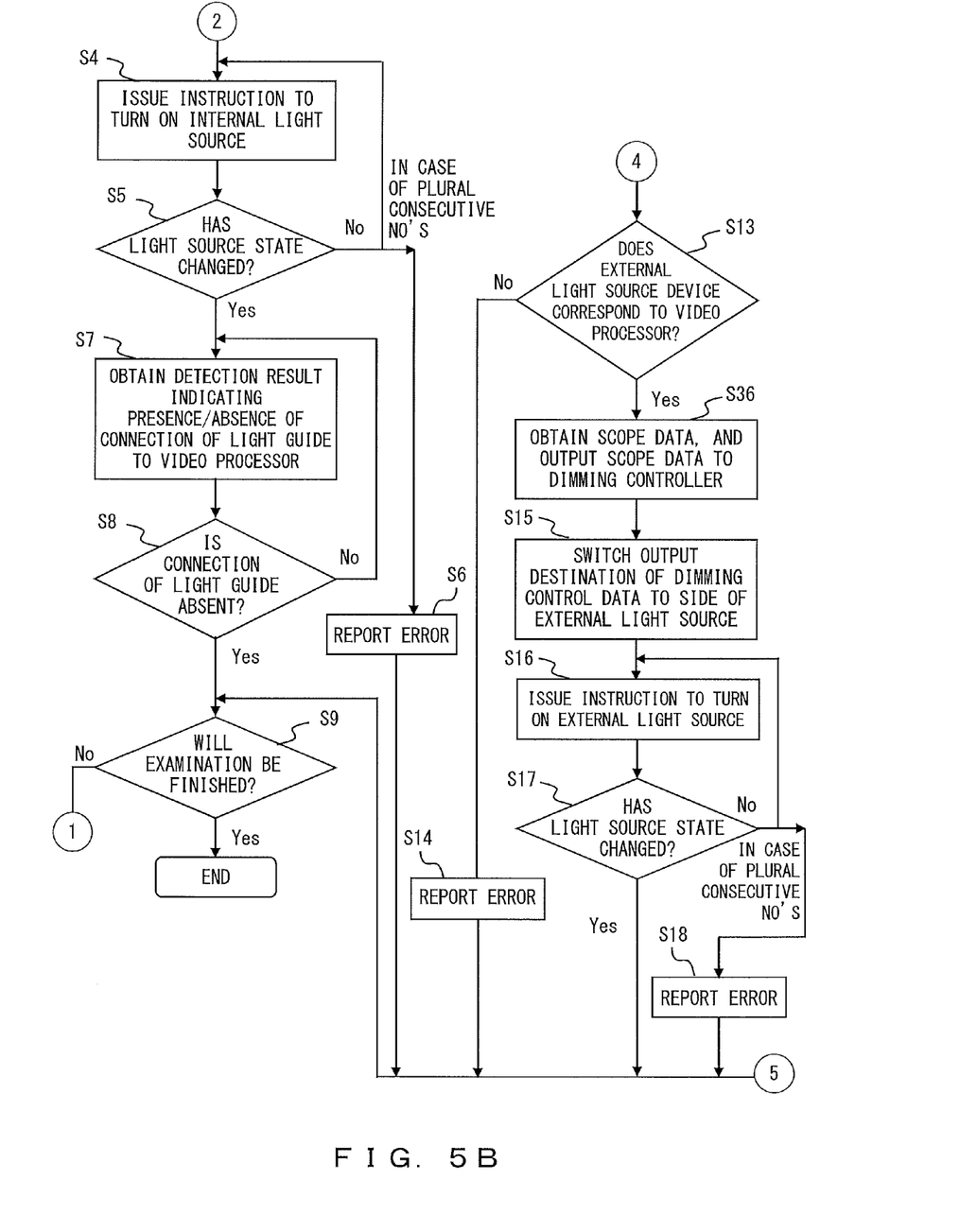
FIG. 5B is a second flowchart illustrating an example of a light source switching operation performed by the light source integrated type video processor that is the video processor according to the second embodiment.
Figure 5C:
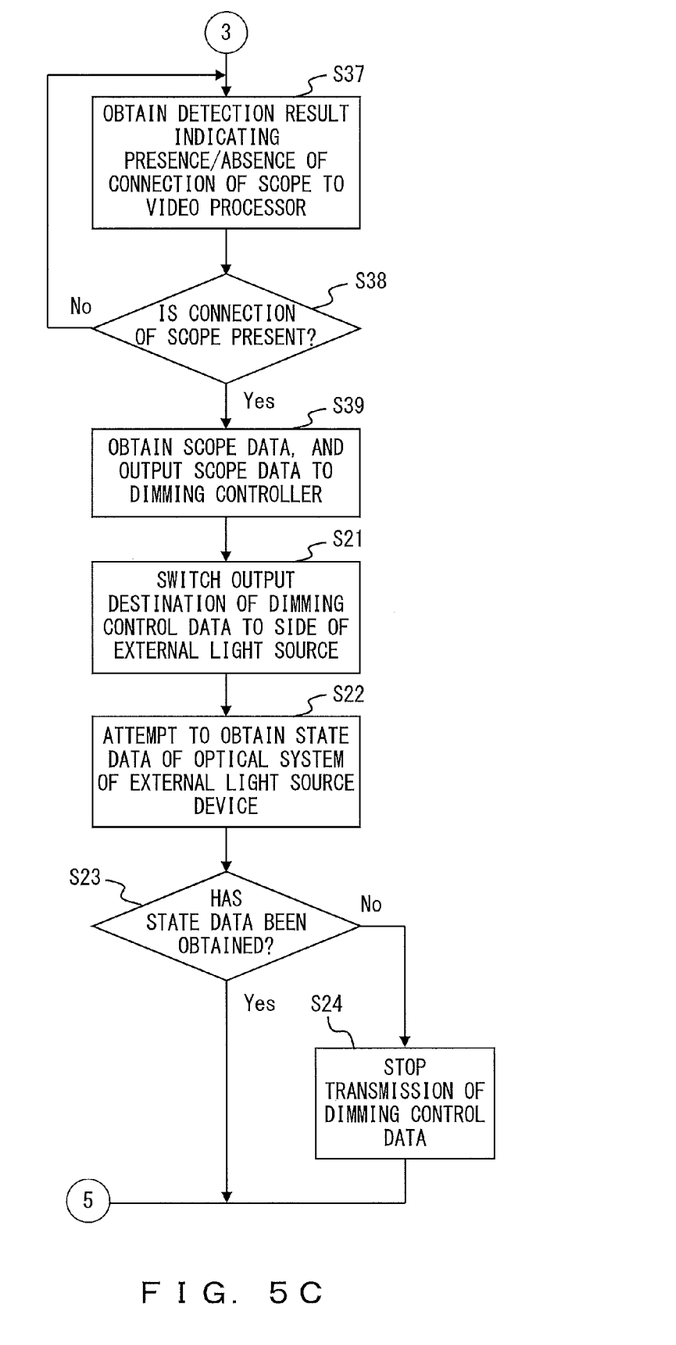
FIG. 5C is a third flowchart illustrating an example of a light source switching operation performed by the light source integrated type video processor that is the video processor according to the second embodiment.

FIG. 5 (FIG. 5A, FIG. 5B, and FIG. 5C) is a flowchart illustrating an example of the light source switching operation.

The operation illustrated in FIG. 5 corresponds to the operation illustrated in FIG. 3, and differences from the operation illustrated in FIG. 3 are described below.

In the operation illustrated in FIG. 5, when the determination result in S2 is Yes, the processes of S31 to S33 are further performed, and the processing moves on to S3. When the determination result in S11 is Yes, the processes of S34 and S35 are further performed, and the processing moves on to S12. When the determination result in S13 is Yes, the process of S36 is further performed, and the processing moves onto S15. When the determination result in S11 is No, the processes of S37 to S39 are further performed, and the processing moves on to S21.

The processes of S31 to S33, the processes of S34 to S36 (S34, S35, and S36), and the processes of S37 to S39 are similar to each other. Therefore, the processes of S31 to S33 are representatively described below, and description of the processes of S34 to S36 and the processes of S37 to S39 is omitted.

In S31 to S33, first, the main controller 305 obtains, from the scope detector 321, a detection result indicating the presence/absence of connection to the scope 200 (200A or 200B) (S31), and determines whether the scope 200 (200A or 200B) is connected to the video processor 300 in accordance with the detection result (S32). When the determination result is No, the processing returns to S31. When the determination result in S32 is Yes, the main controller 305 obtains scope data from the scope 200 (200A or 200B) via the image I/F 301 and the image processing unit 302, and outputs image sensor data included in the scope data to the dimming controller 304 (S33).

In the operation illustrated in FIG. 5, dimming control data in which an output destination is switched to a side of an internal light source in S3 after S33 is dimming control data according to the internal light source that is generated by the dimming controller 304 under the control of the main controller 305 on the basis of the image sensor data that has been input from the main controller 305 in S33 and image data that has been input from the scope 200 (200A or 200B) via the image I/F 301.

In addition, dimming control data in which an output destination is switched to a side of an external light source in S15 after S36 is dimming control data according to the external light source that is generated by the dimming controller 304 under the control of the main controller 305 on the basis of image sensor data that has been input from the main controller 305 in S36, the image data that has been input from the scope 200 (200A or 200B) via the image I/F 301, state data of the optical system 504a of the external light source device 500A, and device data of the external light source device 500A.

Dimming control data in which an output destination is switched to a side of an external light source in S21 after S39 is dimming control data according to the external light source that is generated by the dimming controller 304 under the control of the main controller 305 on the basis of image sensor data that has been input from the main controller 305 in S39, the image data that has been input from the scope 200 (200A or 200B) via the image I/F 301, and state data of the optical system 504b of the external light source device 500B.

The operation illustrated in FIG. 5 is similar to the operation illustrated in FIG. 3 in the other respects.

As described above, by employing the video processor according to this embodiment, it goes without saying that effects similar to those in the video processor according to the first embodiment can be obtained, and dimming control data can be generated in such a way that an amount of illumination light changes according to an image sensor included in a connected scope. Accordingly, as an example, in a case in which an image senor of a scope is a high-pixel-number image sensor, the lifetime of a light source can be prolonged and power consumption can be reduced by generating dimming control data in such a way that an amount of illumination light is smaller than in a case in which the image sensor is a standard-pixel-number image sensor.

Various variations can be made in the respective embodiments above.

As an example, in the video processor 300 according to the respective embodiments, in a case in which a light guide is not connected to the light guide I/F 312, an internal light source (a light source in the video processor 300) is not used. Therefore, in this case, the main controller 305 may perform control such that the power supply to the optical system 311 that is not used is stopped or such that the optical system controller 310 that is not used is shifted to a sleep state. This can prevent the video processor 300 from uselessly consuming power.

As another example, in the video processor 300 according to the respective embodiments, in a case in which a light guide is connected to the light guide I/F 312, and the external light source device 500A is connected to the external device communication I/F 307 and the dimming communication I/F 309, an external light source (a light source of the external light source device 500A) is not used. Therefore, in this case, the main controller 305 may perform control such that the external light source device 500A that is not used is shifted to a sleep state. This can prevent the external light source device 500A from uselessly consuming power.

As yet another example, in the video processor 300 according to the respective embodiments, in a case in which a light guide is connected to each of the light guide I/F 312 of the video processor 300 and the light guide I/F 501 (501*a* or 501*b*) of the external light source device 500 (500A or 500B) connected to the video processor 300, a light source to be used may be configured so as to be manually switchable according to a user's operation of a not-illustrated operation unit in the video processor 300. As an example, in the endoscope system 100 illustrated in FIG. 4, a user may change an observation method from a first observation method in which the scope 200A is used as a scope and an internal light source (a light source in the video processor 300) is used as a light source to a second observation method in which the scope 200B is used as the scope and an external light source (a light source in the external light source device 500A) is used as the light source, and may further change the observation method to the first observation method. In this case, the user may connect the scope 200B to the image I/F 301 in the video processor 300 in a state in which a light guide of the scope 200A that is currently used is connected to the light guide I/F 312, and may connect a light guide of the scope 200B to the light guide I/F 501*a* in the external light source device 500A. In this case, the light guide is still connected to the light guide I/F 312, and in this state, the internal light source is used. The external light source requested by the user cannot be used, and the observation method cannot be changed to the second observation method. Accordingly, in the case above, the user may operate the operation unit of the video processor 300 so as to switch a light source to be used to the external light source.

In addition, as an example, in the video processor 300 according to the respective embodiments, setting information of the external light source device 500A may be obtained and stored while the external light source device 500A is being used. In a case in which the external light source device 500A has broken down and another external light source device 500A or an internal light source (a light source in the video processor 300) is used instead, the other external light source device 500A or the internal light source may be set according to the stored setting information. By doing this, even when an external light source device 500A being used has broken down, another external light source device 500A or an internal light source to be used instead can automatically take over the settings of the broken external light source device 500A. The setting information of the external light source device 500A includes, for example, information relating to setting of special light observation, setting of automatic/manual dimming, or the like.

Further, as an example, the video processor 300 according to the respective embodiments can be configured such that a display according to a function of the external light source device 500A being used can be performed on a not-illustrated front display panel (a liquid crystal display (LCD) with a touch panel) of the video processor 300, and such that the external light source device 500A can be set via the front display panel. Settings at this time of the external light source device 500A may be stored, and the settings may be used when the external light source device 500A has broken down, as described above. Setting of the external light source device 500A that can be performed via the front display panel of the video processor 300 is the same as setting of the external light source device 500A that can be performed via a not-illustrated front display panel (an LCD with a touch panel) of the external light source device 500A, and examples thereof include setting of turning on/off, setting of brightness, setting of a special light observation, and setting of automatic/manual dimming.

As another example, in the respective embodiments, a light source included in the optical system 504*a* of the external light source device 500A may be an infrared light source, and a light source included in the optical system 500*b* of the external light source device 500B may be a stroboscopic light source.

As yet another example, in the respective embodiments, a light source included in the optical system 504*a* of the external light source device 500A may be an LED light source.

As yet another example, in the respective embodiments, the main controller 506*a* of the external light source device 500A may output, to the video processor 300, a detection result of the light guide detector 502*a* that indicates the type of a light guide (such as a light guide for a high luminance or a light guide for a standard luminance), and the detection result may be reported to the dimming controller 304 and the image processing unit 302. The dimming controller 304 may generate dimming control data according to a luminance that the light guide can handle in accordance with the report. In addition, the image processing unit 302 may perform image processing according to the luminance that the light guide can handle in accordance with the report.

As yet another example, in the operation illustrated in FIG. 3 according to the first embodiment, a process similar to the process of S15 (or S21) may be performed instead of the processes of S15 and S21, after the determination result in S2 becomes No before the process of S10 is started. Similarly, in the operation illustrated in FIG. 5 according to the second embodiment, a process similar to the process of S15 (or S21) may be performed instead of the processes of S15 and S21, after the determination result in S2 is No before the process of S10 is started.

As yet another example, in the respective embodiments, white balance data of each light source may be stored in a memory within a scope or the video processor 300, corresponding white balance data may be read from the memory within the scope or the video processor 300 in accordance with a light source being utilized that has been determined by the utilized light source determination unit 305*a*, and white balance processing may be performed according to the data.

As yet another example, in the respective embodiments, the external light source device 500B may be configured so as not to include the dimming communication I/F 505*b*. In this case, dimming control of the external light source device 500B is performed according to settings (such as light amount setting) that are input to the external light source device 500B in an operation directly performed by a user.

When supply of a power output from an external power source is stopped, the video processor receives an OFFP signal indicating stopping of the power supply at the same time as the power supply is stopped. In this case, the video processor may output a black image to a monitor that outputs a video signal such as an endoscopic image, and may cause the monitor to enter into a black display state. This can prevent an unneeded image from being displayed on the monitor when the power source is in the OFF state.

It is assumed that the video processor confirms connection/non-connection to a scope when the power source is in the ON state, and that when the scope is not connected, the video processor records a non-connection log. In a case in which the video processor performs reset processing (power-off processing) when the power source is in the ON state, non-connection information indicating that the scope is not connected is needed even when the scope is connected. Accordingly, upon receipt of a reset processing instruction, the video processor performs reset processing by generating an OFFP signal that indicates reset processing and the non-connection information. However, when the method above is used, a problem arises wherein a non-connection log is recorded in the video processor in accordance with the non-connection information that is generated for reset processing, even when the scope is connected.

Accordingly, when the OFFP signal is generated, the video processor may perform control such that the video processor performs reset processing according to the non-connection information, but stops recording of the non-connection log. This can prevent the non-connection log from remaining as a record, even when the power source is suddenly turned off in a state in which the scope is connected.

The embodiments described above give specific examples of the present invention in order to make the invention easily understandable, and the present invention is not limited to the embodiments described above. Various modifications or variations to the present invention can be made without departing from the spirit of the present invention specified in the claims.

What is claimed is:

1. A video processor that is connectable to an endoscope and an external light source device that supplies illumination light to a light guide of the endoscope, the video processor comprising:
    a connection detector that detects a presence/absence of connection between the video processor and the light guide of the endoscope;
    an internal light source unit that supplies the illumination light to the light guide of the endoscope;
    a communication controller that performs communication with the external light source device, and obtains device data of the external light source device; and
    a utilized light source determination unit that determines a light source that supplies the illumination light to the light guide of the endoscope in accordance with a detection result of the connection detector or a state of obtainment of the device data of the communication controller, wherein
    the utilized light source determination unit performs:
        determining that the internal light source unit is a light source being utilized, when the light guide of the endoscope is connected to the video processor;
        determining that an external light source device that is communicable with the video processor is being utilized, when the communication controller obtains the device data in a state in which the light guide of the endoscope is not connected to the video processor; and
        determining that an external light source device that is not communicable with the video processor is being utilized, when the communication controller fails to obtain the device data in a state in which the light guide of the endoscope is not connected to the video processor.

2. The video processor according to claim 1, further comprising:
    an image processor that processes image data obtained by the endoscope;
    a dimming controller that generates dimming control data that controls an amount of the illumination light supplied to the light guide of the endoscope; and
    a switching unit that switches an output destination of the dimming control data to the internal light source unit when the light guide of the endoscope is connected to the video processor, and that switches the output destination of the dimming control data to the external light source device when the light guide of the endoscope is not connected to the video processor.

3. The video processor according to claim 2, wherein
when the light guide of the endoscope is connected to the video processor, the dimming controller generates the dimming control data according to the internal light source unit, and the switching unit switches the output destination of the dimming control data to the internal light source unit.

4. The video processor according to claim 2, wherein
when the light guide of the endoscope is not connected to the video processor, the dimming controller generates the dimming control data according to the external light source device, and the switching unit switches the output destination of the dimming control data to the external light source device.

5. The video processor according to claim 4, wherein
the dimming controller generates the dimming control data according to the external light source device in accordance with the device data obtained from the external light source device.

6. The video processor according to claim 2, further comprising:
    an endoscopic data obtaining unit that obtains endoscopic data relating to the endoscope connected to the video processor, wherein
    the dimming controller generates the dimming control data according to the endoscopic data.

* * * * *